(12) United States Patent
Gruenke et al.

(10) Patent No.: US 7,416,894 B2
(45) Date of Patent: Aug. 26, 2008

(54) STABLE WATER STANDARD

(75) Inventors: Silke Gruenke, Bremen (DE); Stefanie Bauer, Hoechst i.Odw. (DE)

(73) Assignee: Merck Patent GmbH, Darmstadt (DE)

( * ) Notice: Subject to any disclaimer, the term of this patent is extended or adjusted under 35 U.S.C. 154(b) by 132 days.

(21) Appl. No.: 10/567,553

(22) PCT Filed: Jul. 14, 2004

(86) PCT No.: PCT/EP2004/007777

§ 371 (c)(1),
(2), (4) Date: Feb. 8, 2006

(87) PCT Pub. No.: WO2005/007520

PCT Pub. Date: Feb. 24, 2005

(65) Prior Publication Data

US 2006/0234380 A1    Oct. 19, 2006

(30) Foreign Application Priority Data

Aug. 8, 2003    (DE) ............................. 103 36 571

(51) Int. Cl.
*G01N 33/18* (2006.01)
(52) U.S. Cl. ..................... 436/42; 436/39; 436/174
(58) Field of Classification Search ............. 436/8, 436/19, 39, 42, 174; 252/408.1
See application file for complete search history.

(56) References Cited

U.S. PATENT DOCUMENTS

| | | | | |
|---|---|---|---|---|
| 5,246,863 A | * | 9/1993 | Dahms ........................ 205/788 |
| 5,340,541 A | * | 8/1994 | Jackson et al. ................. 422/75 |
| 6,131,442 A | * | 10/2000 | Krause ........................... 73/73 |
| 6,946,298 B2 | * | 9/2005 | Hoffmann et al. ............. 436/42 |
| 7,049,146 B2 | * | 5/2006 | Miller ........................... 436/42 |
| 7,122,376 B2 | * | 10/2006 | Miller ........................... 436/42 |
| 2004/0171161 A1 | | 9/2004 | Miller | |

FOREIGN PATENT DOCUMENTS

| | | |
|---|---|---|
| EP | 0482465 | 4/1992 |
| JP | 4-297869 | * 10/1992 |
| WO | WO 0240991 | 5/2002 |

OTHER PUBLICATIONS

Neuss J D et al: "Sodium Tartrate Dihydrate as a Primary Standard for Karl Fischer Reagent" Analytical Chemistry, American Chemical Society. Columbus, US Bd. 23, 1951, 1332-1333, XP001042005.

* cited by examiner

*Primary Examiner*—Maureen M Wallenhorst
(74) *Attorney, Agent, or Firm*—Millen, White, Zelano, Branigan, P.C.

(57) ABSTRACT

The invention relates to water standards that are producible by grounding and mixing at least one component abounding in water and one water-free or low water component each. The inventive water standards are characterized by a good storage stability. They are suitable for the calibration or the inspection of devices to determine the water content after thermal release, especially for determining the water content according to Karl Fischer in combination with a Karl Fischer oven (Karl-Fischer oven technique).

17 Claims, No Drawings

STABLE WATER STANDARD

The invention relates to solid water standards having improved stability. Standards of this type having a defined water content are typically employed as calibrators and/or control samples in aquametry using oven techniques. An important field of application is the oven technique in combination with Karl Fischer determination (KF oven technique).

In the Karl Fischer (KF) oven technique, the sample is firstly heated by a freely programmable temperature profile. An inert and dry carrier gas flowing through the sample space takes up the liberated water and transports it into the connected titration cell. The water is determined in the cell filled with Karl Fischer reagent. The determination can be carried out both volumetrically and also coulometrically by the Karl Fischer method.

Karl Fischer reagents essentially comprise iodine (oxidant), sulfur dioxide or salts thereof (reducing agent), a basic component and an alcoholic component. In the reaction, the reducing agent is oxidised by the oxidant with consumption of the water to be determined.

Other potential uses of the solid water standard are thermogravimetric methods or thermal methods in combination with various sensors (for example coulometric based on $P_2O_5$).

Standard substances having a defined water content are required both for quality assurance and also for calibration. Disodium tartrate dihydrate is used as primary standard having a water content of 15.66 (±0.10) percent by weight. EP 0 012 617 describes the use of kaolinite ($Al_2[(OH)_4/Si_2O_5]$; $Al_2O_3.2SiO_2.2H_2O$) having a water content of 15 percent by weight. Also known is the use of sodium tungstate dihydrate as standard substance (water content of 11 percent by weight). In order also to provide standards having a lower water content, other substances are commercially available for this purpose: potassium citrate monohydrate (5.55% by weight of water) or lactose (5% by weight of water). The use of lactose as standard is disclosed in EP 0 482 465 A1. The calibration of a measurement method should preferably be carried out in the vicinity of the proposed working point, i.e. using a standard which has a water content as is to be expected in the measurement samples, for example 1% by weight of water. Such a standard is commercially available: it has a water content of 1% by weight and consists of a mixture of anhydrous sodium tungstate and sodium tungstate dihydrate (see Safety Data Sheet for Cat. No. 188053; Merck KGaA, Darmstadt, Del.). These two substances in different mixtures enable the water content to be set to 10% by weight of water to about 0.1% by weight of water. This water standard thus meets the main requirements of the users, in particular of the Karl Fischer method in combination with a KF oven:
  low water content of 1%
  rapid and complete release of water at temperatures>100° C.
  use in a broad temperature range (high temperature stability, no decomposition below 300° C.).

With the introduction of new instruments for the oven technique (for example Metrohm Oven Sample Processor 774, Mettler Stromboli, ECH Halle KF oven), the demand for an oven standard of this type and the requirements of its quality properties is constantly increasing.

However, it has been found that problems regarding the stability occur on storage of the above-mentioned water standard under extremely unfavourable storage and use conditions. Thus, the object is to provide a water standard having improved stability, where the water content thereof can be set, in particular, in the range from 10% by weight of water to about 0.1% by weight of water, depending on the components used, and which only changes its water content slightly even on open handling or storage in a moist atmosphere (for example greater than 60% relative humidity).

It has been found that the stability of the water standard described above, which consists of a mixture of anhydrous sodium tungstate and sodium tungstate dihydrate, can be considerably improved if potassium sulfate is employed instead of anhydrous sodium tungstate. It has furthermore been found that water standards having improved stability are generally accessible by grinding and mixing at least one stable water-containing compound and at least one stable water-free compound.

The invention relates to solid, pulverulent standards for the determination of water, consisting of at least one stable water-containing compound and at least one stable water-free compound, where the constituents have particle sizes of less than 300 μm. Preferred embodiments have a water content of between 0.005 and 10% by weight. The invention furthermore relates to a process for the preparation of these standards comprising the following working steps:
  a) provision of at least one stable water-containing compound and at least one stable water-free compound;
  b) reduction of the particle size of the constituents mentioned in a) to less than 300 μm;
  c) calculation of the proportions of the stable water-containing compound(s) and of the stable water-free compound(s) in order that the water content desired for the standard arises in the mixture;
  d) mixing of the constituents obtained from step b) in accordance with the proportions calculated in step c), where the sequence of steps b) and c) can be exchanged.

Finally, the invention relates to the use of a solid, pulverulent mixture consisting of at least one stable water-containing compound and at least one stable water-free compound as water standard for the determination of water, in particular by means of the oven technique.

Criteria for the selection of the compounds which are suitable in accordance with the invention are:
  chemically inert
  similar bulk densities
  good miscibility
  melting point>400° C.
  low risk potential with respect to toxicity Preference is given here to inorganic salts. The water standards provided by the present invention are distinguished by high stability, even at elevated atmospheric humidity levels. Furthermore, the water standards according to the invention can be used in a temperature range between 140 and 400° C. Water is released at a high rate at temperatures above 100° C. This enables the water to be liberated from the standard within 5 minutes in the case of sample quantities less than 0.5 g. Analysis times are achieved which are not significantly limited by the liberation kinetics of the release of water.

The bulk densities of the components should not differ excessively from one another. However, the central role for the degree of homogenisation is played by the particle size. It determines on the one hand the quality of the random mixture and on the other hand the flow properties, which in turn influence the mixing. In general, solids having a similar particle size can be mixed well. In the case of greatly differing particle sizes, difficulties occur in the preparation of a homogeneous mixture. At the latest during transport and storage, separation effects are observed. The principal cause here is usually the movement of the fine particles through the coarser particles (percolation). Aspects for the preparation of powder mixtures are known, in particular, to the person skilled in the art from the field of pharmaceuticals and described in relevant handbooks, for example in Hagers Handbuch der pharmazeutischen Praxis [Hager's Handbook of Pharmaceutical Practice], 5th Edition, Springer Verlag, Berlin-Heidelberg 1991. Information of this type can also be found in standard reference works, such as Kirk-Othmer, Encyclopedia of Chemical Technology, 4th Edition, Volume 19, John Wiley &sons, NY 1996, p. 1132.

Under the prerequisite of free-flowing materials, even particle-size differences of less than 2:1 for average particle sizes of 100-200 µm can cause segregation during transport of powder mixtures. In the case of greatly different concentration proportions of two substances in a mixture, not only a similar, but also an increasingly small particle size is thus a prerequisite for a homogeneous mixture. For pharmaceutical powder mixtures having a low medicament active ingredient content, maximum limiting particle sizes are defined, for example, depending on the dose to be set. Furthermore, cohesion and adhesion phenomena influence the behaviour of the mixture. However, the bulk densities of the powders to be mixed also influence the quality of the mixture. Owing to the complexity of the correlations, however, quantitative statements cannot be made here.

For use in the preparation of a water standard according to the invention, the raw materials, preferably in analytically pure (p.a.) quality, are ground so that the particle size is less than 300 µm, preferably less than 150 µm. The proportions of the water-containing and water-free components are weighed out and mixed to homogeneity in accordance with the desired water content of the standard and the water contents of the water-containing component and of the water-free component. Devices and the use thereof for grinding salts or similar solids are known to the person skilled in the art, as are devices and methods for the classification and mixing of powders obtained by grinding.

The weights ($M_1$, $M_2$) of the two components can be calculated as a function of their water content ($W_1$, $W_2$) and the desired water content ($W_P$) and the desired amount of the product ($M_P$) in accordance with the following two equations:

$$M_1*W_1+M_2*W_2=M_P*W_P \quad (I)$$

$$M_1+M_2=M_P \quad (II),$$

in which the index 1 denotes the water-free component, the index 2 the water-containing component and the index P the product, i.e. the standard. For a given introduced weight of the water-free (or low-water) component, the requisite amount of the water-containing component is consequently calculated in accordance with formula III:

$$M_2 = M_1 * \frac{(W_P - W_1)}{(W_2 - W_P)} \quad (III)$$

Besides the preferred potassium sulfate, suitable as the water-free component are in principle salts and metal oxides which only crystallise without water or water inclusion and are not hygroscopic. Examples thereof are: barium sulfate, titanium dioxide (rutile) and calcium phosphate. In principle, it is also possible to use compounds whose water-free form is sufficiently stable compared with the water-containing forms. Instead of the water-free component, stable low-water compounds whose water content is below 5 percent by weight, preferably below 1 percent by weight, are also suitable under certain circumstances. As already mentioned, however, the stability of water-free sodium tungstate in such standards is inadequate since the standards take up water under unfavourable storage conditions (temperatures>25° C. and relative atmospheric humidity>80%). The water-free and water-containing components must not have hygroscopic properties. In connection with the present invention, a water-free component is defined as stable if its absolute water content rises by not more than 0.05% over the course of four weeks on open storage between 15 and 30° C. and relative atmospheric humidities of between 20 and 80%.

Suitable as water-containing component are in principle salts which are in the form of stable, defined hydrates. The water in these compounds is typically bound in stoichiometric ratios as water of crystallisation. Hydrates which are suitable as water-containing component are regarded as thermodynamically stable if their vapour pressure is less than the partial pressure of the water vapour in the air (generally atmospheric humidity). If the vapour pressure of a hydrate is greater than the partial pressure of the water vapour in the air, the water of crystallisation is released to the air, the hydrate decomposes. Besides the preferred sodium tungstate dihydrate, suitable salts are those in which only one hydrate form exists, so that the release of water takes place completely at one temperature, such as, for example, sodium molybdate dihydrate. In the context of the present invention, a water-containing component is defined as stable if its relative water content varies by not more than 10% over the course of four weeks on open storage between 15 and 30° C. and relative atmospheric humidities of between 20 and 80%.

The properties of standards according to the invention is further improved if the substances used for the components can readily be ground to the particle size indicated. The mixed components should furthermore form free-flowing powders and must not agglomerate. In the case of very small particle sizes, free-flowing powders are not obtained, but adhesion forces ensure the exclusion of separation phenomena.

The preferred mixture of potassium sulfate and sodium tungstate dihydrate exhibited the best properties. It does not take up any moisture even on open storage and at elevated atmospheric humidity levels.

It is furthermore known that the separation of powder mixtures can be prevented by additional working steps, such as, for example, granulation.

Even without further comments, it is assumed that a person skilled in the art will be able to utilise the above description in the broadest scope. The preferred embodiments and examples should therefore merely be regarded as descriptive disclosure which is absolutely not limiting in any way.

The complete disclosure content of all applications, patents and publications listed above and below, and of the corresponding application DE 103 36 571.0, filed on 8 Aug. 2003, is incorporated into this application by way of reference.

EXAMPLES

Example 1

Preparation of a Water Standard According to the Invention a) Potassium sulfate for analysis (Cat. No. 105153; Merck KGaA, Darmstadt, DE), and sodium tungstate dihydrate for analysis (Cat. No. 106673; Merck KGaA, Darmstadt, Del.) were each ground in an impact mill (alpine model 100 UPZ) until the particle size was 50 µm or less.

b) The water content of the two salts was determined with the aid of the Karl Fischer oven technique;

Potassium sulfate: sample weight: 0.5 g; water content: 0.03% by weight Sodium tungstate dihydrate: sample weight: 0.05 g; water content: 10.8% by weight.

c) 4550 g of potassium sulfate from step a) were introduced into a powder mixer (WAB, model Turbula), and 450 g of sodium tungstate dihydrate for analysis from step a) were introduced and mixed until the mixture was homogeneous.

A powder mixture having a water content of 1.0% by weight which was suitable as water standard was obtained.

Example 2

Preparation of a Water Standard Conforming to the Prior Art (Comparative Experiment)

a) Sodium tungstate dihydrate for analysis (Cat. No. 106673; Merck KGaA, Darmstadt, Del.) was freed from water of crystallisation by drying for a number of hours at 180° C. The resultant anhydrous salt was ground in a cross beater mill (Alpine model 100 P) until the particle size was 150 μm or less. Untreated sodium tungstate dihydrate for analysis (Cat. No. 106673; Merck KGaA, Darmstadt, Del.) was likewise ground in a cross beater mill (Alpine model 100 P) until the particle size was 150 μm or less.

The water content of the two salts was determined as described in Example 1, and corresponding amounts were mixed in a powder mixer. A powder mixture having a water content of 1.0% by weight which was suitable as water standard was obtained.

Example 3

Comparative Experiment Storage Stability

Aliquots of approx. 100 g of the materials obtained in accordance with Examples 1 and 2 were each stored in 1 l polyethylene powder bottle with screw cap (F) and aliquots of 1 g were each stored in 3 open sample vials (O). The water content was in each case determined by means of the Karl Fischer oven technique after preparation and after 24 and 28 weeks. In each case 3 determinations were carried out per standard substance (in each case 1 sample per open vessel (O) and a triple determination from the closed bottle (F)).

Instrument: 774 KF oven processor and 756 KF coulometer with diaphragm cell

Parameters: for oven: T=150° C., flow rate 70 ml/min
for coulometer: extraction time 300 sec, relative stop drift<20 μg/min, automatic drift correction
Sample weight: 50-200 mg The storage was carried out at room temperature. During the initial time period, the room temperature was between 18 and 25° C. with a relative atmospheric humidity of below 60%. The room temperature was subsequently up to 30° C. with an atmospheric humidity of up to 80%. The results are shown in Table 1 below.

TABLE 1

Comparative experiment storage stability

| Material/Storage | Initial value | 24 weeks | 28 weeks |
|---|---|---|---|
| Example 1; | 1.0386 | 1.0885 | 1.0471 |
| Storage F | 1.0342 | 1.0977 | 1.0547 |
|  | 1.0266 | 1.0988 | 1.0535 |
| Average: | 1.0331 | 1.0950 | 1.0518 |
| (%) | 100.0 | 106.0 | 101.8 |
| Example 1; | 1.0386 | 1.0668 | 1.0741 |
| Storage O | 1.0342 | 1.0368 | 1.0581 |
|  | 1.0266 | 1.0353 | 1.0594 |
| Average: | 1.0331 | 1.0463 | 1.0639 |
| (%) | 100.0 | 101.3 | 103.0 |
| Example 2 (p.a.); | 0.9893 | 0.9965 | 0.9604 |
| Storage F | 0.9999 | 0.9683 | 0.9679 |
|  | 0.9905 | 0.9842 | 0.9751 |
| Average: | 0.9932 | 0.9830 | 0.9665 |
| (%) | 100.0 | 99.0 | 97.3 |
| Example 2 (p.a.); | 0.9893 | 1.0052 | 2.1661 |
| Storage O | 0.9999 | 1.0217 | 2.1790 |
|  | 0.9905 | 1.0463 | 2.1120 |
| Average: | 0.9932 | 1.0244 | 2.1524 |
| (%) | 100.0 | 103.1 | 216.7 |

Example 4

Homogeneity of the Mixture

The mixture prepared in accordance with Example 1 was shaken for 20 min in a shaking machine in a filled 100 ml PE bottle and then investigated for any separation effects that had occurred. To this end, 5 samples of each of the upper and lower fractions were taken for the determination of water. No separation phenomena were observed.

Parameters for the determination: see Example 3
Results:
Upper fraction: (0.967+/−0.002) % of water
Lower fraction: (0.968+/−0.006) % of water

The invention claimed is:

1. A method for the determination of water comprising determining the water content in a sample using a Karl Fischer oven technique with a water standard comprising a mixture of at least one stable water-containing compound and at least one inorganic, stable water-free compound.

2. A method according to claim 1, wherein said mixture is a free flowing powder.

3. A method according to claim 1, wherein the water-free compound and the water-containing compound have melting points>400° C.

4. A method according to claim 1, wherein the determination of water is conducted at a temperature range between 140 and 300° C.

5. A method according to claim 1, wherein said water-free compound is an inorganic compound.

6. A method according to claim 1, wherein said standard has a water content of between 0.005 and 10% by weight.

7. A method according to claim 1, wherein said standard comprises a mixture of potassium sulfate and sodium tungstate dihydrate.

8. A method for the determination of water in a sample comprising:
determining the water content of said sample with Karl Fischer oven technique using a water standard comprising a mixture of at least one stable water-containing compound and at least one inorganic stable water-free compound where the water-containing and water free compounds have particle sizes of less than 300μm.

9. A method according to claim 8, wherein said water standard has a water content of between 0.005 and 10% by weight.

10. A method according to claim 9, wherein said water-containing compound is sodium tungstate dihydrate.

11. A method according to claim 9, wherein said water-containing compound is sodium molybdate dihydrate.

12. A method according to claim 9, wherein said standard has a water content of between 0.1 and 10% by weight.

13. A method according to claim 8, wherein said water-free compound is potassium sulfate.

14. A method according to claim 8, wherein said water-free compound is barium sulfate, titanium dioxide (rutile) or calcium phosphate.

15. A method according to claim 8, wherein said water-containing and water-free compounds have particle sizes of less than 150 μm.

16. A method according to claim 15, wherein said water-containing and water-free compounds have particle sizes of less than 50 μm.

17. A process for the preparation of a water standard, comprising:
   a) providing at least one stable water-containing compound and at least one inorganic stable water-free compound;
   b) reducing the particle size of the compounds in a) to less than 300 μm;
   c) calculating the proportions of the stable water-containing compound(s) and of the stable water-free compound(s) in order that the water content desired for the standard arises;
   d) mixing the compounds obtained from step b) in accordance with the proportions calculated in step c),
   where the sequence of steps b) and c) can be exchanged.

* * * * *